US012597499B2

(12) United States Patent
Felber et al.

(10) Patent No.: US 12,597,499 B2
(45) Date of Patent: *Apr. 7, 2026

(54) TRANSMISSION OF DATA ASSOCIATED WITH AN INJECTION DEVICE USAGE USING PASSIVE RF MODULATION

(71) Applicant: Sanofi, Paris (FR)

(72) Inventors: Matthias Felber, Wil (CH); Nathanael Wettstein, Wil (CH); Felix Kramer, Wil (CH)

(73) Assignee: Sanofi, Paris (FR)

( * ) Notice: Subject to any disclaimer, the term of this patent is extended or adjusted under 35 U.S.C. 154(b) by 142 days.

This patent is subject to a terminal disclaimer.

(21) Appl. No.: 18/449,028

(22) Filed: Aug. 14, 2023

(65) Prior Publication Data

US 2023/0410974 A1      Dec. 21, 2023

Related U.S. Application Data

(63) Continuation of application No. 16/955,893, filed as application No. PCT/EP2018/085110 on Dec. 17, 2018, now Pat. No. 11,769,578.

(30) Foreign Application Priority Data

Dec. 21, 2017     (EP) .................................... 17306866

(51) Int. Cl.
*G16H 20/17*      (2018.01)
*A61M 5/31*      (2006.01)
*A61M 5/315*      (2006.01)

(52) U.S. Cl.
CPC ......... *G16H 20/17* (2018.01); *A61M 5/31511* (2013.01); *A61M 5/31566* (2013.01);
(Continued)

(58) Field of Classification Search
CPC .......... A61M 5/31511; A61M 5/31566; A61M 2005/3125; A61M 2205/3389; A61M 2205/3592; A61M 2205/3561
See application file for complete search history.

(56) References Cited

U.S. PATENT DOCUMENTS 5,471,147 A     11/1995  Allen et al.
7,935,088 B2     5/2011  Veasey et al.
(Continued)

FOREIGN PATENT DOCUMENTS

CA          2689017          11/2002
CN          1102253 A          5/1995
(Continued)

OTHER PUBLICATIONS

International Preliminary Report on Patentability in International Appln. No. PCT/EP2018/085110, dated Jun. 23, 2020, 7 pages.
(Continued)

*Primary Examiner* — Bradley J Osinski
(74) *Attorney, Agent, or Firm* — Fish & Richardson P.C.

(57) ABSTRACT

Implementations of the present disclosure are directed to an injection device including: a reservoir including a wall defining a proximal end, a distal end and a tubular side, a plunger rod configured to be movable within the reservoir in a direction from the distal end to the proximal end, a radio frequency (RF) antenna attached to the tubular side and configured to receive an interrogation signal from an external device, and a resonating assembly configured to receive the interrogation signal from the RF antenna and to generate a modulated RF signal having a frequency associated with a position of the plunger rod.

23 Claims, 9 Drawing Sheets

(52) U.S. Cl.
    CPC .............. *A61M 2005/3125* (2013.01); *A61M*
              *2205/3389* (2013.01); *A61M 2205/3592*
              (2013.01); *A61M 2205/8206* (2013.01)

(56)                References Cited

U.S. PATENT DOCUMENTS

| | | | |
|---|---|---|---|
| 2001/0034506 A1 | 10/2001 | Hirschman et al. |
| 2004/0171983 A1 | 9/2004 | Sparks et al. |
| 2005/0015055 A1 | 1/2005 | Yang |
| 2009/0043253 A1 | 2/2009 | Podaima |
| 2009/0217774 A1 | 9/2009 | Sills et al. |
| 2009/0318876 A1 | 12/2009 | Hansen et al. |
| 2010/0191186 A1 | 7/2010 | Blumberg, Jr. et al. |
| 2010/0292685 A1 | 11/2010 | Katoh et al. |
| 2011/0152825 A1 | 6/2011 | Marggi |
| 2011/0264033 A1 | 10/2011 | Jensen et al. |
| 2012/0074957 A1 | 3/2012 | Schroeder |
| 2013/0149172 A1 | 6/2013 | Butterfield et al. |
| 2013/0310756 A1 | 11/2013 | Whalley et al. |
| 2014/0214001 A1 | 7/2014 | Mortazavi |
| 2014/0221914 A1 | 8/2014 | Calasso |
| 2015/0018771 A1 | 1/2015 | Schenker et al. |
| 2015/0174330 A1 | 6/2015 | Nagel et al. |
| 2016/0259913 A1 | 9/2016 | Yu et al. |
| 2017/0147918 A1 | 5/2017 | Karani et al. |
| 2017/0316157 A1 | 11/2017 | Riedel et al. |
| 2021/0085879 A1 | 3/2021 | Ploch et al. |
| 2021/0104309 A1 | 4/2021 | Felber et al. |

FOREIGN PATENT DOCUMENTS

| | | | |
|---|---|---|---|
| CN | 101189497 | A | 5/2008 |
| CN | 101268336 | | 9/2008 |
| CN | 101484783 | A | 7/2009 |
| CN | 103961765 | | 8/2014 |
| CN | 103961765 | A | 8/2014 |
| CN | 104321096 | | 1/2015 |
| CN | 104428688 | A | 3/2015 |
| CN | 104661696 | | 5/2015 |
| CN | 105999481 | | 10/2016 |
| DE | 102010041572 | B3 | 3/2012 |
| EP | 2764881 | | 8/2014 |
| EP | 3244947 | | 10/2021 |
| IN | 4363CHN2014 | A | 9/2015 |
| JP | 2008-212665 | | 9/2008 |
| WO | WO 2006/108026 | | 10/2006 |
| WO | WO 2007/039148 | | 4/2007 |
| WO | WO 2007/116863 | | 10/2007 |
| WO | WO 2009/024562 | | 2/2009 |
| WO | WO 2014/033195 | | 3/2014 |
| WO | WO 2016/113348 | | 7/2016 |
| WO | WO 2017/016959 | | 2/2017 |
| WO | WO 2017/021227 | | 2/2017 |

OTHER PUBLICATIONS

International Search Report and Written Opinion in International Appln. No. PCT/EP2018/085110, dated Feb. 1, 2019, 9 pages.

300

Start

Receive wake signal
302

Generate activation signal
304

Generate RF signal
306

Transmit RF signal
308

Receive modulated RF signal
310

Process modulated RF signal
312

Display injection device data
314

TRANSMISSION OF DATA ASSOCIATED WITH AN INJECTION DEVICE USAGE USING PASSIVE RF MODULATION

BACKGROUND

Electronic injection devices allow patients to safely administer a medicament, without the need for constant supervision by medical staff, while enabling transmission of treatment data to the medical staff. Electronic injection devices can include a medicament reservoir like a cartridge or syringe, an electric component, a drive system, and an energy supply. The electronic component can be configured to detect the usage of the electronic injection device and to transmit the data. The usage detection and data transmission can require a significant amount of energy supply. The energy supply can be provided by a battery. However, a low battery condition can lead to no- or malfunction of the electronic injection device, an incorrect dosage, a missed dosage, or it can even make the electronic injection device unusable by stopping the operation of the electronic components.

SUMMARY

Implementations of the present disclosure include injection devices and systems using passive radio frequency (RF) signals to transmit injection device data. In some implementations, an injection device includes a reservoir including a wall defining a proximal end, a distal end and a side wall, a plunger rod configured to be movable within the reservoir in a direction from the distal end to the proximal end, the injection device having a tubular side being defined by either a housing component, an inner or outer body component, or the medicament reservoir, a radio frequency (RF) antenna attached to the tubular side and configured to receive an interrogation signal from an external device, and a resonating assembly configured to receive the interrogation signal from the RF antenna and to generate a modulated RF signal having a frequency associated with a position of the plunger rod. In some implementations, the resonating assembly includes a magnet attached to the plunger rod and one or more resonators attached to the tubular side and configured to change their RF characteristics based on at least one of a linear and angular position relative to the magnet. In some implementations, the resonating assembly includes a mechanical link attached to the plunger rod and a strain sensitive resonator attached to the tubular side, the strain sensitive resonator being configured to change its RF characteristics based on at least one of a linear and angular position relative to the mechanical link. In some implementations, the mechanical link includes at least one of a spring, an eccentric element, and an eccentric disc. In some implementations, the resonating assembly includes a mechanical link attached to the plunger rod and an oscillator attached to the tubular side, the oscillator being configured to change its RF characteristics based on at least one of a linear and angular position relative to the mechanical link. In some implementations, the mechanical link includes a beam that is attached through a membrane to a cantilever of the oscillator. In some implementations, the resonating assembly includes a multi-slot patch resonator such that the RF signal includes at least one of an identifier of the injection device and a medicament type. In some implementations, the interrogation signal includes a plurality of interrogation signals received at regular time intervals. In some implementations, in response to receiving the plurality of interrogation signals, the resonating assembly generates a plurality of RF signals, such that a frequency shift between two of the plurality of RF signals is associated with an amount of medicament within the reservoir. In some implementations, the interrogation signal is generated in response to a trigger signal transmitted by the injection device. In some implementations, the position of the plunger rod is indicative of an amount of medicament within the reservoir.

In accordance with another aspect of the present disclosure, a medicament injection system includes: an external device and an injection device. The external device includes: a transmitter configured to generate an interrogation signal, a receiver configured to receive a radio frequency (RF) signal, and one or more processors configured to process the RF signal and to generate result data to be displayed by the external device. The injection device includes a reservoir including a wall defining a proximal end, a distal end and a tubular side, a plunger rod configured to be movable within the reservoir from the distal end to the proximal end, a RF antenna attached to the tubular side and configured to receive an interrogation signal from an external device, and a resonating assembly configured to receive the interrogation signal from the RF antenna and to generate the RF signal having a frequency associated with a position of the plunger rod.

In some implementations, the resonating assembly includes a magnet attached to the plunger rod and one or more resonators attached to the tubular side and configured to change their RF characteristics based on at least one of a linear and angular position relative to the magnet. In some implementations, the resonating assembly includes a mechanical link attached to the plunger rod and a strain sensitive resonator attached to the tubular side, the strain sensitive resonator being configured to change its RF characteristics based on at least one of a linear and angular position relative to the mechanical link. In some implementations, the mechanical link includes at least one of a spring, an eccentric element, and an eccentric disc.

It is appreciated that systems in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Figure 1A:
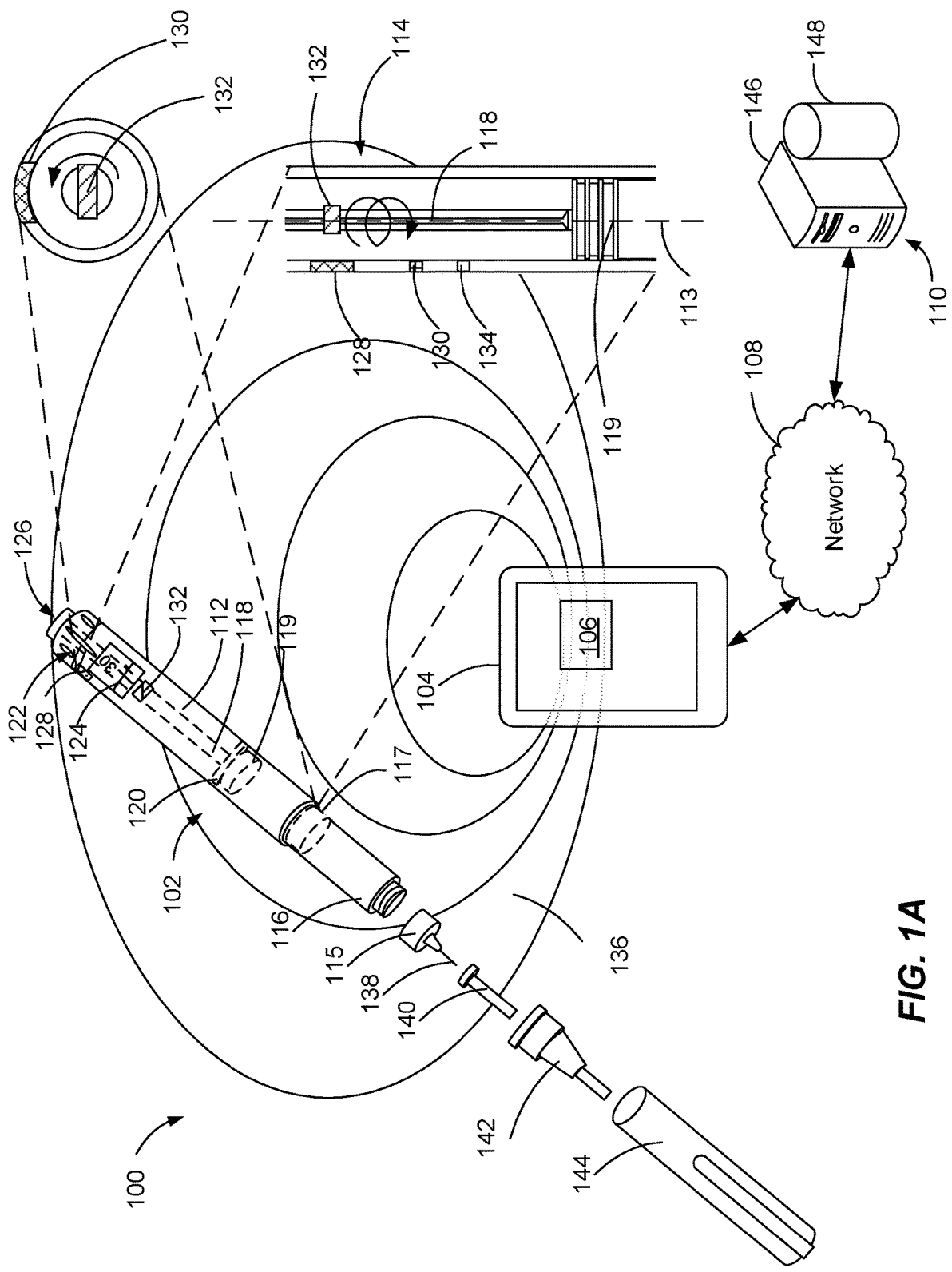
FIGS. 1A-1F are exploded views of examples of systems in accordance with the present disclosure.

Implementations of the present disclosure are generally directed to mechanisms and systems configured for measuring an amount of medicament within injection devices. More particularly, implementations of the present disclosure are directed to a technique for using passive transmission of modulated radio frequency (RF) signals to determine a volume of a medicament reservoir.

Among other things, we describe techniques for powering an injection device without, for example, using a battery. In some injection devices, transmission of injection device data is based on technologies such as Bluetooth, ANT+ or passive RF identifier/near field communications that can be associated with high power consumption. As described in further detail herein, implementations of the present disclosure address this challenge. For example, in accordance with implementations, the injection device has the sensing functionality integrated into the RF-circuit and transfers the sensing information by analog approach without requiring a battery or a wired connection for energy supply. The injection device does not require energy harvesting or energy conversions for the injection device or for communication, which enables meter-long communication range. The transmission technology allows a simple system setup on injection device side. The components of the injection device do not have an impact on the user operation of the injection device. For example, the patient does not have to replace batteries, or plug in the injection device for RF signal transmission. An electronic injection device configured to operate without a battery has a low environmental footprint and can be manufactured as a disposable item.

FIGS. 1A-1F illustrate exploded views of example medicament delivery systems 100. The example medicament delivery systems 100 can be configured to facilitate sharing of medical data using passive RF transmission. The example medicament delivery systems 100 can include one or more injection devices 102, an external device 104, an interrogator 106, a network 108, and a server system 110.

In some implementations, the injection device 102 a pre-filled, disposable injection pen, and in some implementations, the injection device 102 is a reusable injection pen. The injection device 102 is configured to communicate with the interrogator 106. For example, the injection device 102 can be configured for frequency-based interrogation and the interrogator 106 can transmit frequency-based signals received from the injection device 102 to the external device 104. In some implementations, the frequency-based signals are transmitted from the injection device 102 to the external device 104 using time-domain reflectometry. In some implementations, the injection device 102 can be associated with an identifier that is used by the external device 104 to uniquely identify the injection device 102, for example, because the identifier is specific to the external device 104.

The injection device 102 can be configured to modulate a RF signal received from the interrogator 106 based on an amount of medicament stored within the injection device 102. The injection device 102 can be a pre-filled, disposable injection pen or the injection device 102 can be a reusable injection pen. The injection device 102 can include a housing 112 and a needle assembly 115. The injection device 102 can include one or more tubular sides defining any of an inner wall or an outer wall of a component of the injection device 102, such as the housing 112 or a medicament container such as a medicament reservoir 116. The housing 112 can contain a RF modulation system 114, the medicament reservoir 116, a stopper 117, a plunger rod 118, a plunger head 119, a bearing 120, a dosage knob 122, a dosage window 124, and an injection button 126. The housing 112 can be molded from a medical grade plastic material such as a liquid crystal polymer.

The RF modulation system 114 can include one or more electronic components configured to modulate RF signals received from the interrogator 106 and transmit modulated RF signals to the interrogator 106. For example, the RF modulation system 114 can include an antenna 128, a resonator 130, a moving element 132 and a sensor 134.

The antenna 128 can be configured to communicate with the interrogator 106 by receiving and transmitting modulated RF signals while being within the communication field 136. The antenna 128 can be configured for passive RF transmission. For example, the antenna 128 can be a meander-line dipole antenna. The modulated RF signals transmitted by the antenna 128 can include an indication of the amount of the medicament in the medicament reservoir 116, values measured by a sensor 134, and the identifier of the injection device 102.

The resonator 130 (resonating assembly) can be configured to modulate RF signals received by the antenna 128. The resonator 130 can include one or more resonators aligned along a longitudinal axis 113 of the housing 112. The resonator 130 can include one of a plurality of types of resonators, such as mechanical type, magnetic type, or microelectromechanical type.

The moving element 132 can be configured to be attached to the plunger rod 118, which advances in micro-step increments to dispense a particular amount of medicament. The moving element 132 can include one or more moving elements directly or indirectly attached to the plunger rod 118. The moving element 132 can include one or more of a plurality of types of moving elements, such as mechanical type, magnetic type, or microelectromechanical type. In some implementations, the type of the resonator 130 can depend on the type of the moving element 132.

The example RF modulation system 114 illustrated in FIG. 1A includes a resonator 130 based on a metamaterial attached to a wall of the housing 112 and a moving element 132 that includes a magnet directly attached to or inserted in the plunger rod 118. In some implementations, the magnet is attached to the last dose nut. Metamaterials include a class of materials configured to have a particular set of properties. Typically, the properties are not present in the base material, but are resulting from the specific microstructure or structured combination of the materials used. In accordance with implementations described herein, the metamaterials are defined as materials configured to exhibit a specific response by changing one or more of their inherent properties when a physical or chemical stimulus is applied. The external stimuli may be strain, magnetic field, temperature, humidity and pressure. Within the context of the example of FIG. 1A, the metamaterial of resonator 130 can include magnetic thin films or magnetic composites that are configured to modulate RF signals depending on the applied magnetic field. The resonance frequency of the resonator 130 can be shifted depending on an angular position, a linear position or a combination of linear and angular position of the moving element 132 (magnet) relative to the resonator 130. Angular and/or linear displacement of the moving element 132 (magnet) is associated with a frequency shift. To determine a dose of medicament within the injection device 102, the frequency shift is being read by the interrogator 106 at regular time intervals.

Figure 1B:
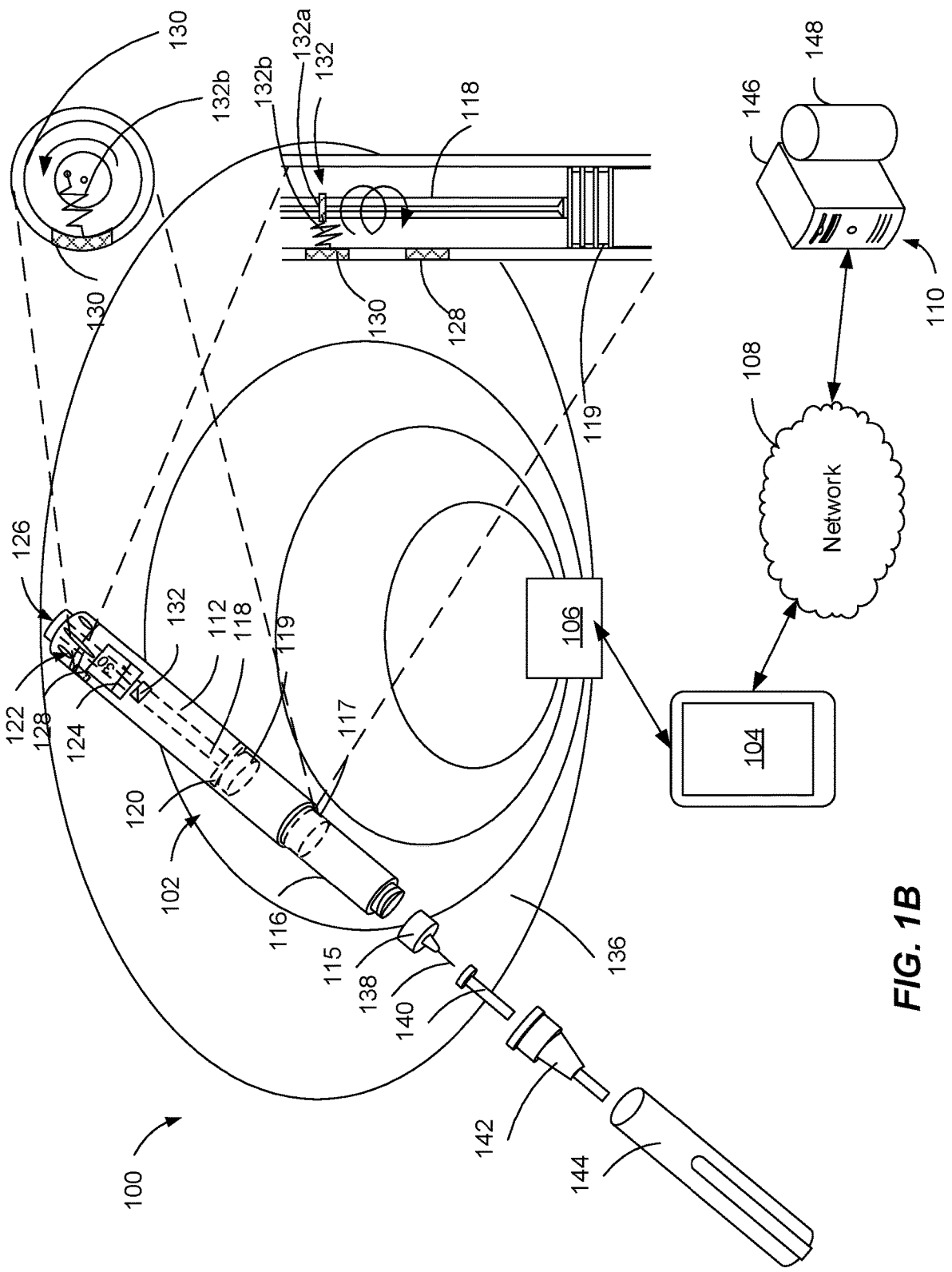

The example RF modulation system 114 illustrated in FIG. 1B includes a strain sensitive resonator 130 attached to a wall of the housing 112 and attached to the moving element 132. The strain sensitive resonator 130 can include a strain sensitive metamaterial, such as polytetrafluoroethylene (PTFE). The moving element 132 includes an attachment base 132a and a spring stretched between the attachment base 132a and moving element 132. The attachment base 132a is attached to or inserted in the plunger rod 118. The resonance frequency of the strain sensitive resonator 130 can be shifted depending on the force associated with an angular position, a linear position or a combination of linear and angular position of the moving element 132 (attachment base 132a) relative to the resonator 130. Angular and/or linear displacement of the moving element 132 (attachment base 132a) is associated with a variation of the elastic force within the spring 132b and a frequency shift. To determine a dose of medicament within the injection device 102, the frequency shift is being read by the interrogator 106 at regular time intervals (e.g., every few milliseconds).

Figure 1C:
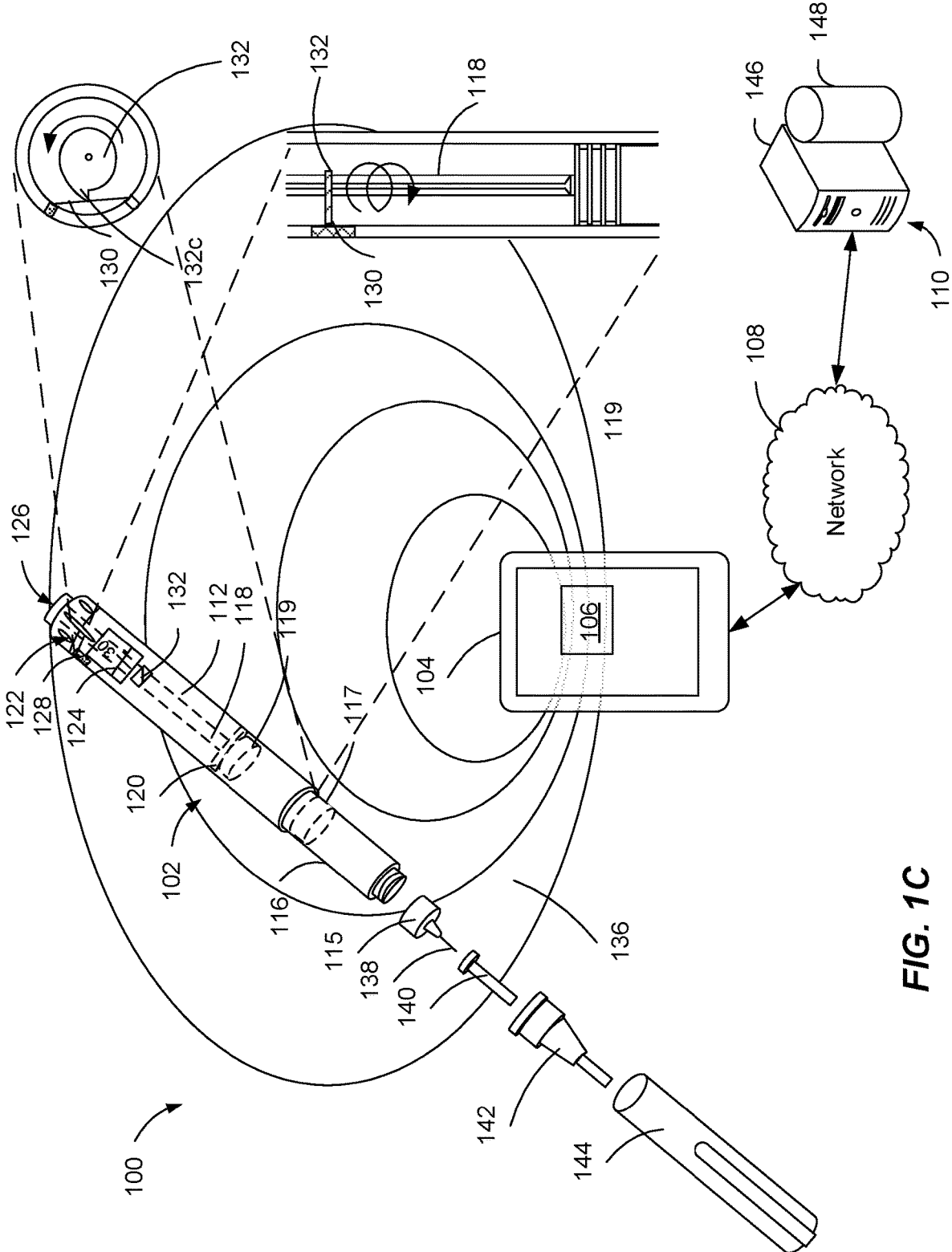

The example RF modulation system 114 illustrated in FIG. 1C includes a strain sensitive resonator 130 attached to a wall of the housing 112 and attached to the moving element 132. The strain sensitive resonator 130 can include a strain sensitive metamaterial, such as polytetrafluoroethylene (PTFE). The moving element 132 can include a disc with an eccentric element 132c attached to the plunger rod 118. The resonance frequency of the strain sensitive resonator 130 can be shifted depending on the force associated with an angular position, a linear position or a combination of linear and angular position of the moving element 132 relative to the resonator 130. For example, depending on the angular and/or linear location of the eccentric element 132c a particular pressure level can be exercised on the strain sensitive resonator 130, which converts the pressure to a frequency shift. To determine a dose of medicament within the injection device 102, the frequency shift is being read by the interrogator 106 at regular time intervals.

Figure 1D:
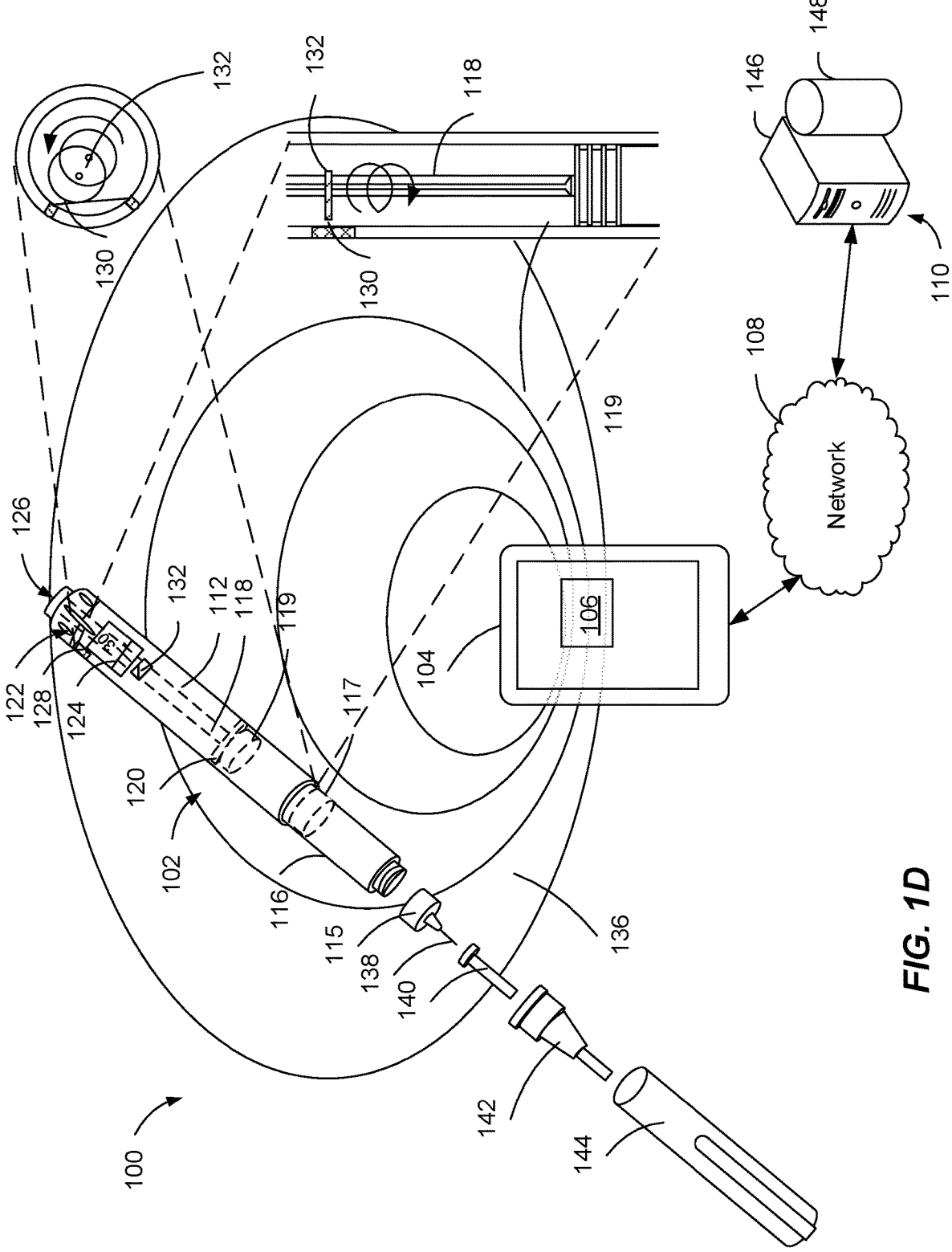

The example RF modulation system 114 illustrated in FIG. 1D includes a strain sensitive resonator 130 attached to a wall of the housing 112 and attached to the moving element 132. The strain sensitive resonator 130 can include a strain sensitive metamaterial, such as polytetrafluoroethylene (PTFE). The moving element 132 can include an eccentric wheel attached to the plunger rod 118. The resonance frequency of the strain sensitive resonator 130 can be shifted depending on the force associated with an angular position, a linear position or a combination of linear and angular position of the moving element 132 relative to the resonator 130. For example, depending on the angular and/or linear location of the moving element 132 (e.g., an edge of the eccentric wheel) a particular pressure level can be exercised on the strain sensitive resonator 130, which converts the pressure to a frequency shift. To determine a dose of medicament within the injection device 102, the frequency shift is being read by the interrogator 106 at regular time intervals.

Figure 1E:
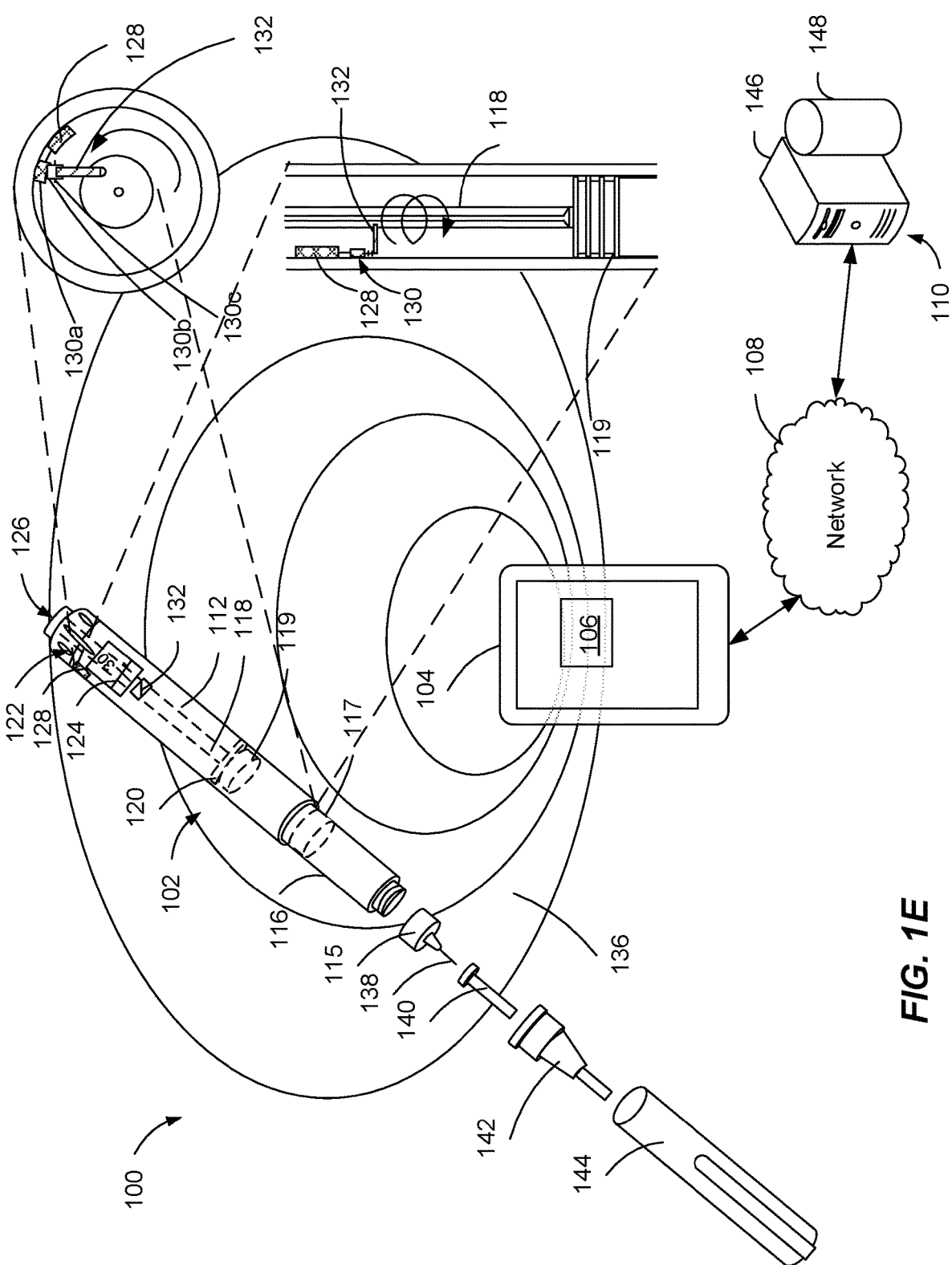

The example RF modulation system 114 illustrated in FIG. 1E includes a resonator 130 attached to a wall of the housing 112 and a moving element 132. The resonator 130 can include a microelectromechanical system (MEMS) oscillator 130a, a cantilever 130b and a membrane 130c. The moving element 132 includes a beam attached to the plunger rod 118 and coupled over the membrane 130c to the resonator 130. The resonance frequency of the strain sensitive resonator 130 can be shifted depending on the force associated with an angular position, a linear position or a combination of linear and angular position of the moving element 132 (beam) relative to the oscillator 130a. Angular and/or linear displacement of the moving element 132 (beam) is associated with a variation of the angle of the cantilever 130b, which induces a frequency shift. To determine a dose of medicament within the injection device 102, the frequency shift is being read by the interrogator 106 at regular time intervals.

Figure 1F:
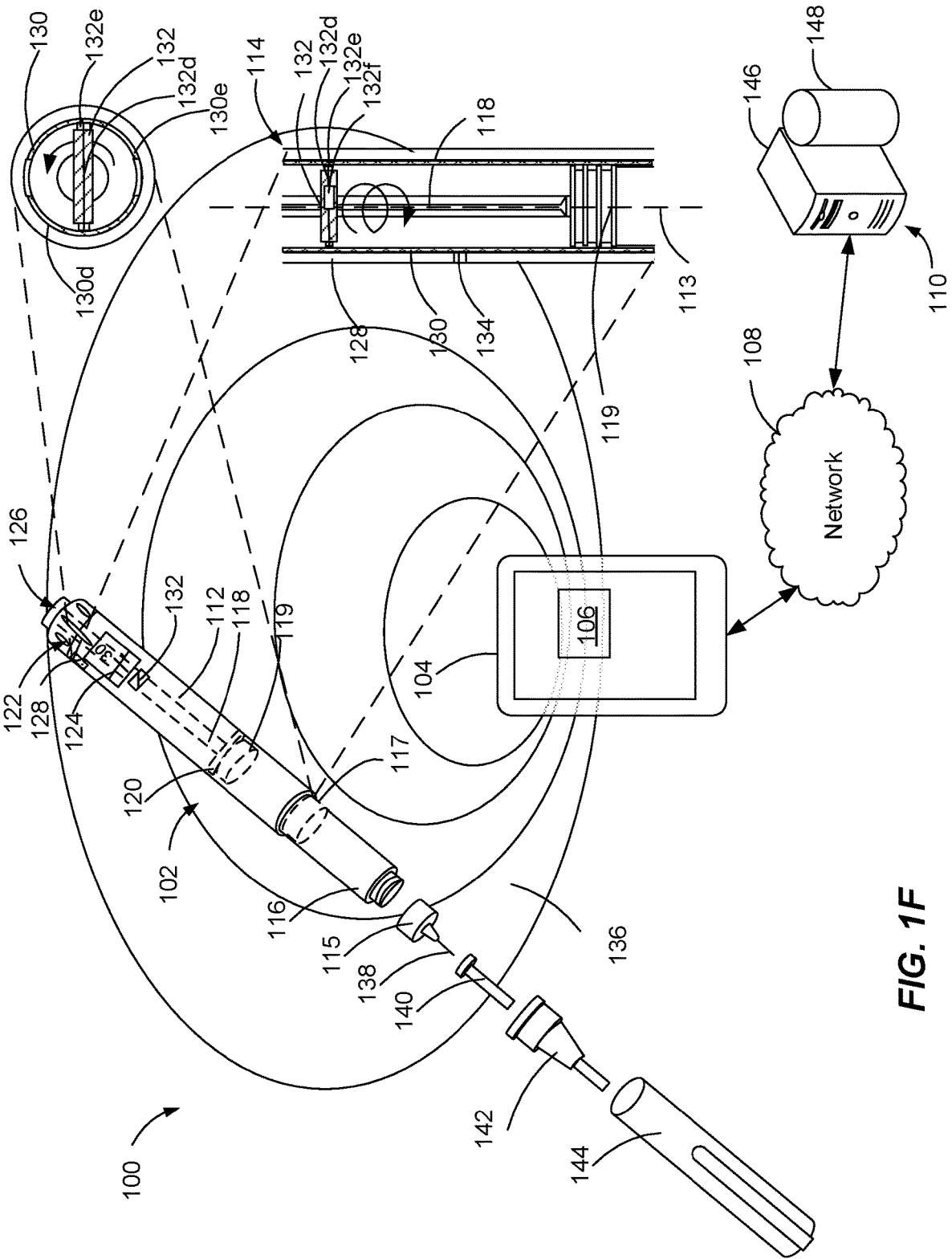

The example RF modulation system 114 illustrated in FIG. 1F includes a resonator 130 defining an electrical circuit attached to a wall of the housing 112 and a moving element 132 that includes the last dose nut directly attached to the plunger rod 118. The electrical circuit can be a thin foil including a printed circuit configured to change its electric properties based on the position of the moving element 132. The moving element 132 (the last dose nut) includes an electric conductor 132d and a pair of brushes 132e. In some implementations, the moving element 132 (the last dose nut) includes an electric element 132f, such as a smart circuit or a load. The electric conductor 132d can be configured to connect to the resonator 130 and the electric element 1321. The electric conductor 132d can short-circuit the resonator 130, can add or change a load or impedance of the resonator 130 or can connect or disconnect segments of the electric circuit 130d, 130e. The pair of brushes 132e can be configured to provide mechanical stability during the position change of the moving element 132. The electric properties of the resonator 130 can change depending on an angular position, a linear position or a combination of linear and angular position of the moving element 132 (the last dose nut) relative to the resonator 130. Angular and/or linear displacement of the moving element 132 (the last dose nut) is associated with a change of the electric properties (e.g., load, impedance, closed or open circuit). To determine a dose of medicament within the injection device 102, the change of the electric properties is being read by the interrogator 106. The interrogator 106 can read the signals associated to the electric properties at regular time intervals by either time-domain reflectometry or phase-encoding transmission principle.

The sensor 134 can be configured to generate a RF signal modulation indicating a parameter including an environmental condition and/or a medicament type. The environmental condition can include temperature, humidity and luminosity. The sensor 134 configured to detect an environmental condition can include a resonator based on a metamaterial or a MEMS resonator. For example, a metamaterial including one or more of phenanthrene (temperature threshold sensing), ionic plastic crystal, metal oxide (e.g. ZnO) can be configured to detect a temperature of the injection device 102. In particular, phenanthrene can be configured to detect a temperature threshold. A metamaterial including one or more of kapton and polyvinyl alcohol (PVA) can be configured to detect humidity of the environment around the injection device 102. The medicament type can be coded using a multi-slot patch resonator. The resonance frequency of the multi-slot patch resonator depends on the number of slots, the slot geometry, the slot width, the slot height and the slot length. The identifier of the injection device 102 can also be coded with a multi-slot patch resonator. The identifier of the injection device 102 can be a unique identifier enabling the identification of the injection device 102 in use. To reduce the number of required bits, it can also be a sufficiently large number, which can be combined with other information (such as medicament type, date, geo-location) to identify the injection device 102 currently within the communication field 136 of the interrogator 106. In some implementations, multiple injection devices 102 are issued with the same "unique" identifier based on one or more rules that prevent two injection devices 102 are issued with the same "unique" at any time to share the same communication field. For example, the injection devices 102 are issued with the same "unique" identifier are sold in different regions of the world, such as, in the European Union and in the United States of America. As another example, identifiers of the injection devices 102 can be repeated after a particular time interval, such as after the expiration duration of the medication included in the injection device 102.

In some implementations, the components of the RF modulation system 114 can be integrated within the housing 112 at a single location, or at multiple locations (e.g., within or attached to a bearing 120 plunger rod 118, and a cavity in the plunger head 119). The location of one or more electronic components of the RF modulation system 114, such as the resonator 130 and/or the moving element 132 can be selected to maximize efficiency of RF signal modulation. The components of the RF modulation system 114 can be molded, fitted or welded to particular components of the injection device 102 (e.g., the housing 112 or the plunger rod 118).

The medicament reservoir 116 can be configured to contain a fluid medicament. The medicament reservoir 116 can be a conventional, generally cylindrical, disposable container like a cartridge or a syringe used to package prepared fluids such as medicaments, anesthetics and the like. The medicament reservoir 116 has a tubular side with an inner wall and an outer wall and two ends. One end (proximal end) has a pierceable membrane, which receives an inward end of needle 138 in sealing engagement. The other end (distal end) can be configured to enable the insertion of the stopper 117.

A dose of the contained medicament can be ejected from the injection device 102 by turning the dosage knob 122, and the selected dose is then displayed via dosage window 124, for instance in multiples of so-called International Units (IU), wherein one IU is the biological equivalent of about 45.5 micrograms of pure crystalline medicament (1/22 mg). An example of a selected dose displayed in dosage window 124 may for instance be 30 IUs, as shown in FIG. 1A. In some implementations, the selected dose can be displayed differently, for instance by an electronic display (e.g., the dosage window 124 may take the form of an electronic display). Turning the dosage knob 122 can cause a mechanical click sound to provide acoustical feedback to a user. The numbers displayed in dosage window 124 can be printed on a sleeve that is contained in housing 112 and mechanically interacts with a plunger head 119 that is fixed at the end of the plunger rod 118 and pushes the stopper 117 within the medicament reservoir 116. The bearing 120 can provide firm mounting to one or both ends of the plunger rod 118.

The plunger head 119 (e.g., a back end of the plunger) can be configured to expel a portion of the fluid by displacing the stopper 117 contained within the medicament reservoir 116, such that a position of the last dose nut, of the plunger rod 118, and of the stopper 117 is associated with an amount of the fluid within the injection device 102. The stopper 117 can be a flexible stopper such as a rubber stopper. The stopper 117 can be of a sufficient length such that the stopper 117 is not ripped or twisted when being engaged by the plunger head 119.

The needle assembly 115 includes a needle 138 that can be affixed to the housing 112. The needle 138 can be covered by an inner needle cap 140 and an outer needle cap 142, which in turn can be covered by an exterior cap 144. When needle 138 is stuck into a skin portion of a patient, and then injection button 126 is pushed, the medicament dose displayed in display window 124 can be ejected from injection device 102. When the needle 138 of injection device 102 remains for a certain time in the skin portion after the injection button 126 is pushed, a high percentage (e.g., more than 95%) of the dose is actually injected into the patient's body. Ejection of the medicament dose can generate a mechanical click sound, which can be different from the sounds produced when using dosage knob 122.

Injection device 102 can be used for several injection processes until either the medicament reservoir 116 is empty or the expiration date of injection device 102 (e.g., 28 days after the first use) is reached. Before using injection device 102 for the first time, it may be necessary to perform a priming operation to remove air from medicament reservoir 116 and needle 138. For instance, the priming operation can include selecting two units of medicament and pressing injection button 126 while holding injection device 102 with the needle 138 upwards. The impulse generated by selecting two units of medicament or pressing injection button 126 can trigger the modulation of RF signals with the RF modulation system 114.

In some implementations, the external device 104 can include the interrogator 106, and in some implementations, the external device 104 can be removably attached to the interrogator 106. The interrogator 106 can be configured to transmit signals to the injection device 102 and receive signals from the injection device 102. The interrogator 106 can be configured to spontaneously transmit signals to the injection device 102 at a pre-set frequency (e.g., between 0.1 Hz and 1 Hz) during pre-set time intervals (e.g., during scheduled treatment time intervals or after receiving an activation signal until two consecutive RF modulated signals are identical). The external device 104 can be configured to process the modulated RF signals transmitted by the injection device 102 and to transmit them over the network 108 to the server device 110.

In some implementations, the server device 110 includes at least one server 146 and at least one data store 148. The server device 110 is intended to represent various forms of servers including, but not limited to a web server, an application server, a proxy server, a network server, and/or a server pool. In general, server systems accept requests for application services and provide such services to any number of client devices (e.g., the external device 104) over the network 108 to support monitoring of usage of the injection device 102. In some implementations, a user (such as a patient or a healthcare provider) can access the application services to analyze past and present data associated with the usage of the injection device 102. The past and present data associated with the usage of the injection device 102 can include dates of medicament injection, expelled doses per date and remaining amount of medicament within the injection device 102.

Figure 2:
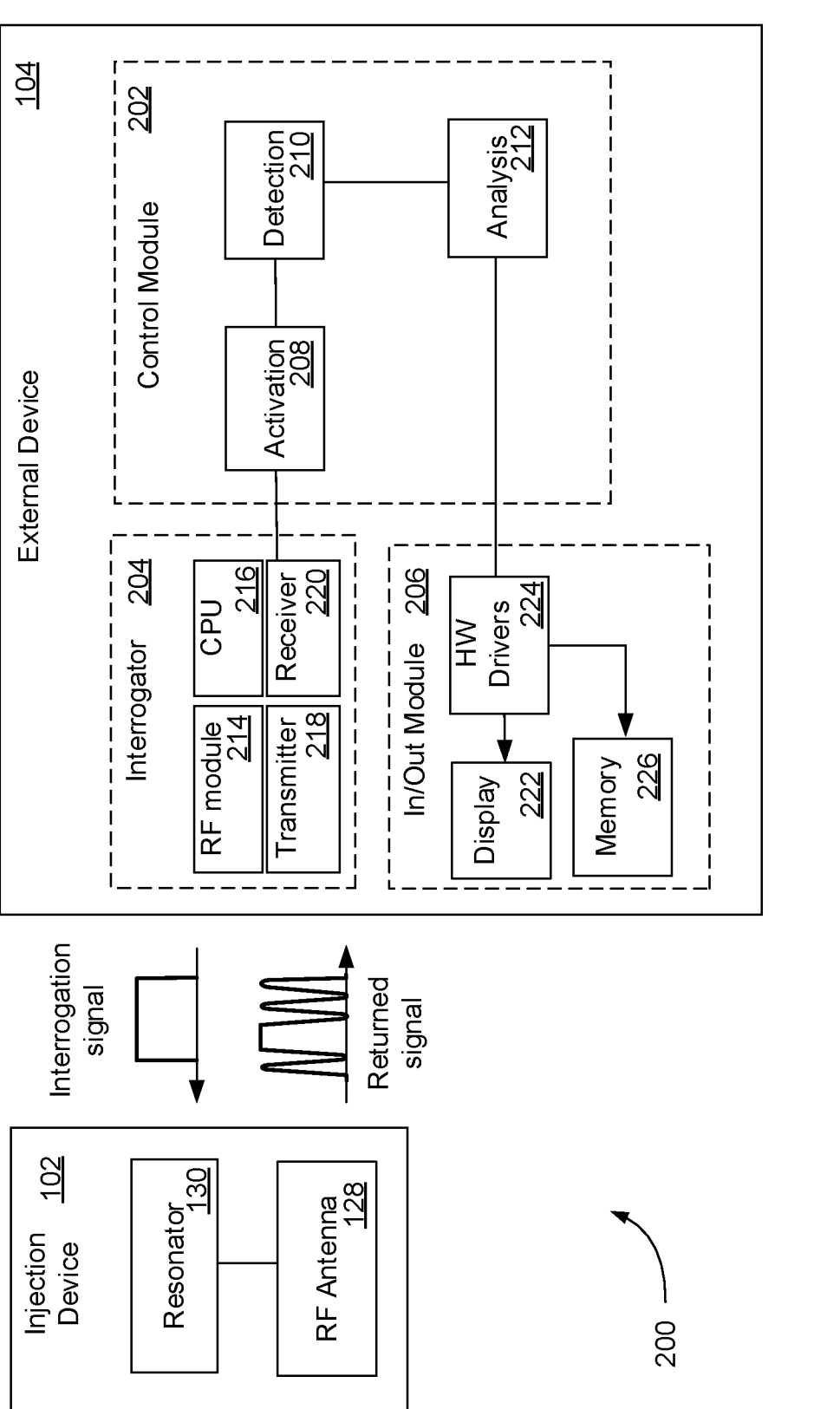
FIG. 2 is a block diagram of an example system architecture that can execute implementations of the present disclosure.

FIG. 2 is a block diagram of an example system 200 that can execute implementations of the present disclosure. The system 200 enables transmission of RF signals between an injection device 102 and an external device 104. The injection device 102 can include an antenna 128 and a resonator 130. The antenna 128 is configured for receiving RF signals from the external device 104. The resonator 130 is configured to passively modulate the RF signals as described in detail with reference to FIGS. 1A-1E. The external device 104 includes a control module 202, an interrogator 204 and an in/out module 206. The control module 202 can be an application downloadable from a server that is configured to control one or more operations of the external device 104. For example, the operation of the external device 104 is controlled by programs executed by the control module 202. The control module 202 includes an activation component 208, a detection component 210 and an analysis component 212.

The activation component 208 can be configured to generate an activation signal that can start a RF communication process with the injection device 102, as described with reference to FIG. 3. The activation of the RF communication process is an important factor contributing to the energy consumption of the external device 104, the usability and the reliability of the detection in the proximity of the external device 104. In some implementations, the activation signal is generated in response to receiving a wake signal. The wake signal can include a word spoken by a user of the external device 104 or a specific noise generated by an operation of the injection device 102 (e.g., a noise associated with a priming operation, a dose dialing click or a dispense click). In some implementations, the activation signal is generated in response to receiving a user input from the in/out module 206 that includes a request to initiate the RF communication process with the injection device 102. In some implementations, the activation signal is generated at a preset frequency (e.g., once or multiple times a day) that can be updated by a user of the external device 104 to correspond with a treatment schedule. The activation signal can include a trigger signal that is transmitted to the interrogator 204 to initiate the RF communication process. The activation signal can include a trigger signal that is transmitted to an energy source (e.g., a battery of the external device) to power the interrogator 204 to initiate the RF communication process. In some implementations, prior to activating the RF communication process, the activation component 208 provides a user of the external device 104, though the in/out module 206, with a message requesting approval to initiate the RF communication process with the injection device 102.

The detection component 210 can be configured to generate a detection signal to control the detection of modulated RF signals using the interrogator 204. In some implementations, the detection process can be controlled based on one or more parameters of the activation process. For example, the detection component 210 can be configured to communicate with the activation component 208 to initiate detection operations at a particular time after the activation component 208 generated the trigger signal. The detection operations can include a pre-processing phase (e.g., echo cancellation and/or noise suppression) and an actual detection phase. In some implementations, the detection component 210 activates a filter (e.g., a bandpass and/or a band-reject filter) included in the external device 104 during the detection of the modulated RF signal.

The analysis component 212 can be configured to generate an analysis signal to control the analysis of modulated RF signals detected by the interrogator 204. For example, the analysis component 212 can control the selection of a signal-processing algorithm. The signal processing algorithm can include one or a combination of basic signal processing methods (e.g., discrete Fourier transform, short-time Fourier transform, discrete cosine transform, discrete-time wavelet transform), short- and mid-term feature extraction, classifiers (e.g., k-nearest-neighbor classifier, decision tree, support vector machine, artificial neural network, deep neural network), algorithms based on a-priori knowledge of the expected signal to 'train' the algorithm and algorithms based on a-priori knowledge of the expected signal to correlate received signals with expected signals to determine regions of interest.

The interrogator 204 can be a component integrated in or attached to the external device 104. The interrogator 204 includes a RF module 214, a CPU 216, a transmitter 218 and a receiver 220. The RF module 214 is configured to generate a RF signal. In some implementations, one or more characteristics of the RF signals are selected based on the resonator 130 of the injection device 102. For example, a pulse signal can be generated for time-domain reflectometry, a signal with a broad frequency range can be generated for the resonator 130 configured to produce frequency modulation, a band-limited pulse signal can be generated for the resonator 130 configured to produce phase modulation or a signal with multiple closely located frequencies (e.g., two frequencies $f_1$ and $f_2$) can be generated for the resonator 130 configured to produce intermodulation (e.g., harmonic frequencies $n*f_1 \pm m*f_2$). The CPU 216 is configured to interpret and execute the control signals (e.g., the activation signal, the detection signal and/or the processing signal) received from the control module 202 and to process the modulated RF signal according to an algorithm selected by the analysis component 212. The transmitter 218 is configured to transmit the RF signal generated by the RF module 214. The receiver 220 is configured to receive the modulated RF signal generated by the injection device 102.

The output module 206 can be a standard component of the external device 104 that is controlled by the control module 202 to support the RF communication with the injection device and the processing of the modulated RF signals. The output module 206 includes a display 222, a hardware driver 224 and a memory 226. The display 222 can be configured to enable a user of the external device 104 to interact with the external device 104 by providing user input and receiving indications associated with the injection device 102 and the treatment performed using the injection device 102. The hardware driver 224 includes a program that controls the display 222. The memory 226 can be a computer-readable medium configured to store data, including modulated RF signals received by the interrogator 204 and results of processing the modulated RF signals.

Figure 3:
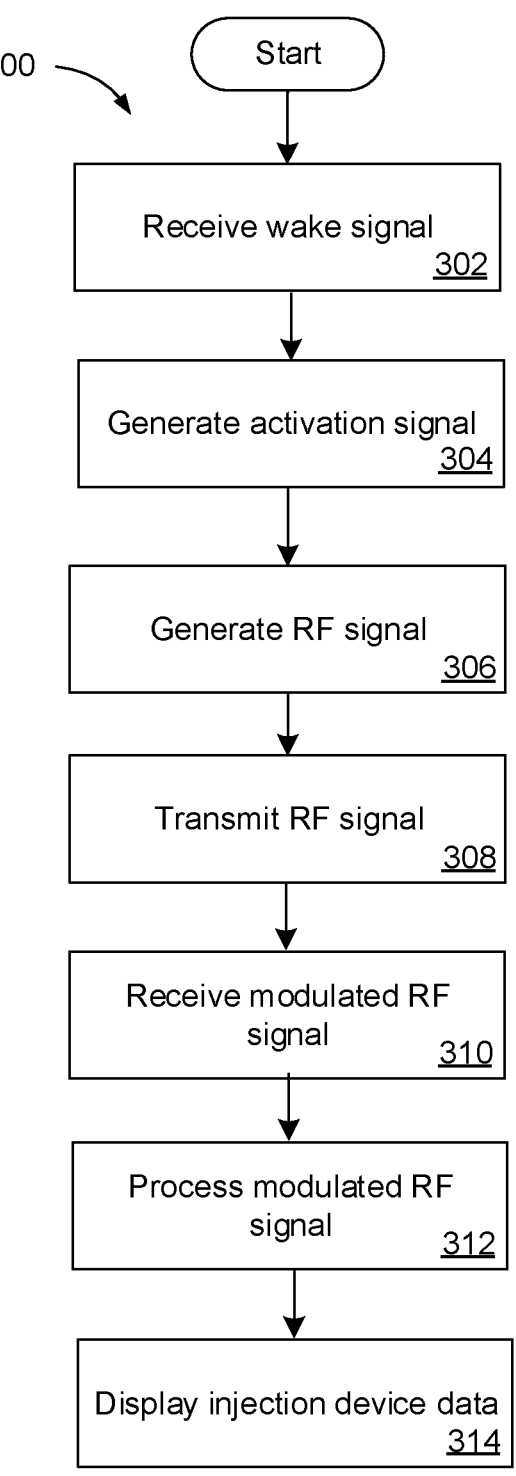
FIG. 3 is a flowchart illustrating an example process that can be executed to perform operations of the present disclosure.

FIG. 3 is a flowchart illustrating an example process 300 that can be executed by devices and systems described with reference to FIGS. 1 and 2. For example, the process 300 can be executed by system 100 of FIGS. 1A-1E or system 200 of FIG. 2. The process 300 begins by receiving a wake signal (302). The wake signal can include a user input indicating a request to initiate the RF communication process between the external device and the injection device 102. The wake signal can be a verbal command (e.g., word spoken by a user of the external device), a user selection (e.g., launching an associated application) or a specific noise generated by an operation of the injection device 102 (e.g., a noise associated with a priming operation, a dose dialing click or a dispense click). An example of a priming operation performed with the injection device can include selecting a particular number (e.g., one or two) of units of medicament and pressing an injection button while holding the injection device with the needle upwards. Another example of a priming operation performed with the injection device can include pressing a priming button of the injection device configured to generate a wake signal. Another example of a priming operation performed with the injection device can include attaching an interrogator to the external device.

In response to receiving the wake signal, an activation signal is generated (304). The activation signal can include one or more trigger signals that are transmitted to one or more components of the external device (e.g., an interrogator, an energy source, and an in/out module). For example, the activation signal can include a trigger signal that is transmitted to the interrogator integrated in or attached to the external device to initiate the RF communication process with the injection device. The activation signal can include a trigger signal that is transmitted to an energy source (e.g., a battery of the external device) to power the interrogator to initiate the RF communication process. Further, the activation signal can include a trigger signal that is transmitted to the in/out module, to retrieve a user approval to initiate the RF communication process with the injection device.

In response to receiving the activation signal, one or more interrogation signals are generated by a RF module of the interrogator (306). The interrogation signal can include a RF signal with particular characteristics. In some implementations, one or more frequency characteristics of the interrogation signals are selected based on a resonator type of a targeted injection device. For example, the interrogation signal can include a pulse RF signal, a broad frequency range RF signal, a band-limited pulse signal RF signal or a RF signal with multiple closely located frequencies. In some implementations, multiple interrogation signals are generated to enable a detection of an amount of medicament dispersed by the injection device.

The interrogation signal is transmitted by the transmitter to the injection device (308). In response to each interrogation signal, a modulated RF signal generated by the resonator of the injection device is received (310). For example, if multiple interrogation signals were transmitted, multiple modulated RF signals are received. The modulated RF signal can include a time-domain modulation, a frequency modulation, a phase modulation or an intermodulation. The modulation of the modulated RF signal indicates a position of a resonator relative to another (mechanical) component of the injection device (e.g., last dose nut, plunger rod, plunger head, and stopper) that is associated with an amount of medicament within the medicament reservoir. In some implementations, if multiple modulated RF signals are received, a frequency shift between two (consecutive) RF signals is associated with an amount of medicament within the reservoir. The modulation of the modulated RF signal can indicate one or more measurements of environmental parameters (e.g., humidity and temperature).

The modulated RF signals are processed by a processor of the external device (312). The processing of the modulated RF signal includes determining injection device data, such as one or more parameters associated with the administration of the medicament (e.g., volume of remaining medicament within the injection device and/or volume of dispensed medicament) and operational conditions of the injection device. The processing of the modulated RF signal can include one or a combination of basic signal processing methods (e.g., discrete Fourier transform, short-time Fourier transform, discrete cosine transform, discrete-time wavelet transform), short- and mid-term feature extraction, classifiers (e.g., k-nearest-neighbor classifier, decision tree, support vector machine, artificial neural network, deep neural network), algorithms based on a-priori knowledge of the expected signal to 'train' the algorithm and algorithms based on a-priori knowledge of the expected signal to correlate received signals with expected signals to determine regions of interest that differentiate between multiple resonators that are integrated in the injection device. The injection device data can be stored, transmitted to another system or displayed to a user of the external device (314). In some implementations, a user interacting with the display of the external device can select to terminate the communication between the injection device and the external device or to repeat the process 300, by generating another wake signal.

Figure 4:
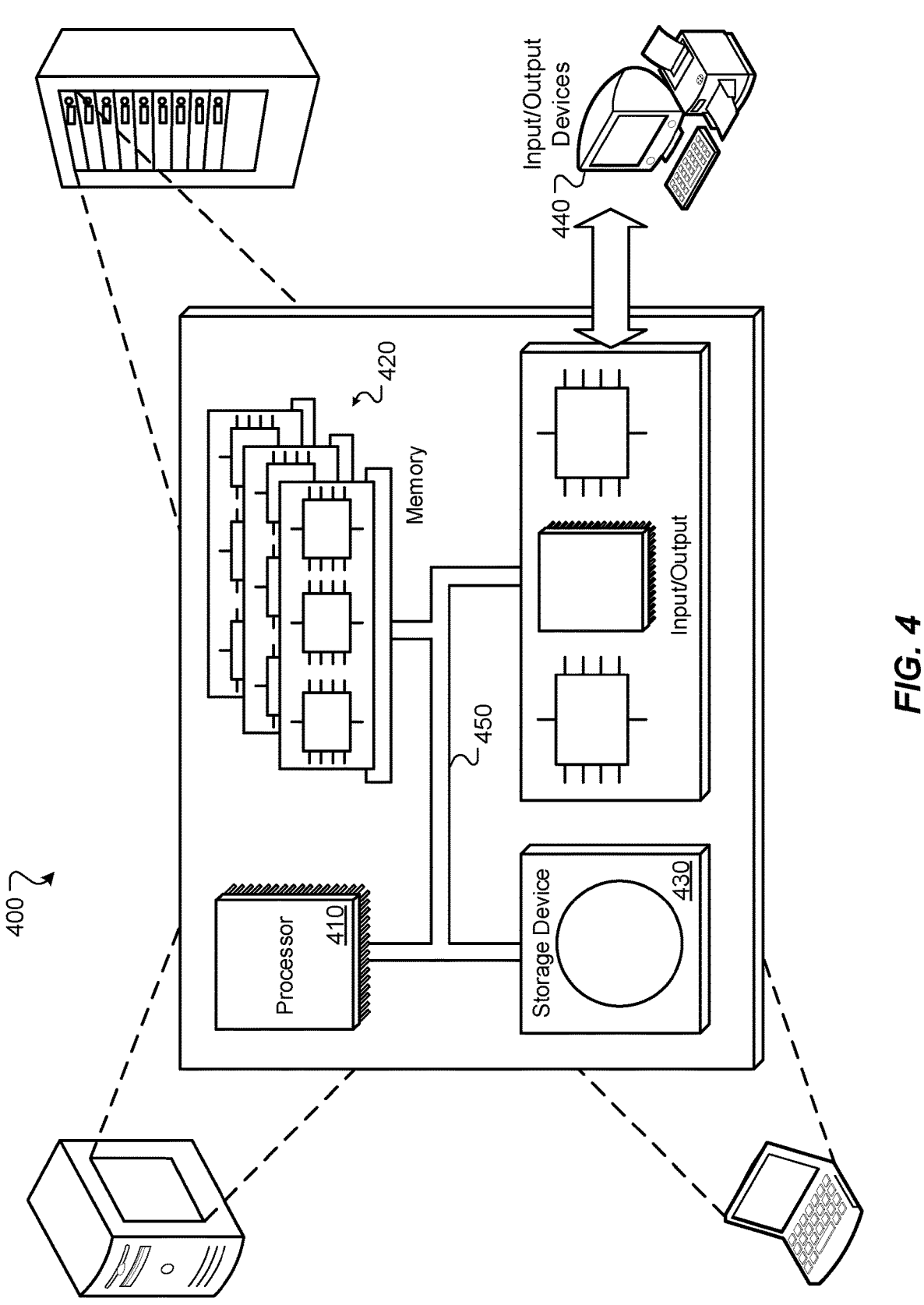
FIG. 4 is a schematic illustration of example computer systems that can be used to execute implementations of the present disclosure.

FIG. 4 shows a schematic diagram of an example computing system 400. The system 400 can be used for the operations described in association with the implementations described herein. For example, the system 400 may be included in any or all of the server components discussed herein. The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit. The storage device 430 is capable of providing mass storage for the system 400. In one implementation, the storage device 430 is a computer-readable medium. In various different implementations, the storage device 430 may be a floppy disk device, a hard disk device, an optical disk device, or a tape device. The input/output device 440 provides input/output operations for the system 400. In one implementation, the input/output device 440 includes a keyboard and/or pointing device. In another implementation, the input/output device 440 includes a display unit for displaying graphical user interfaces that enable a user to access data related to an item that is collected, stored and queried as described with reference to FIGS. 1-3.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases.

Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. An injection device comprising:
a reservoir comprising a wall defining a proximal end, a distal end and a tubular side;
a plunger rod configured to be movable within the reservoir in a direction from the distal end to the proximal end;
a radio frequency (RF) antenna attached to the tubular side and configured to receive an interrogation signal from an external device; and
a resonating assembly configured to receive the interrogation signal from the RF antenna and to generate a modulated RF signal in response to the interrogation signal, the RF signal having a frequency associated with a position of the plunger rod,
wherein the interrogation signal comprises a plurality of interrogation signals received at regular time intervals, and
wherein, in response to receiving the plurality of interrogation signals, the resonating assembly generates a plurality of RF signals, such that a frequency shift between two of the plurality of RF signals is associated with an amount of medicament within the reservoir.

2. The injection device of claim 1, wherein the resonating assembly comprises a magnet attached to the plunger rod and one or more resonators attached to the tubular side and configured to change their RF characteristics based on at least one of a linear and angular position relative to the magnet.

3. The injection device of claim 1, wherein the resonating assembly comprises a mechanical link attached to the plunger rod and a strain sensitive resonator attached to the tubular side, the strain sensitive resonator being configured to change its RF characteristics based on at least one of a linear and angular position relative to the mechanical link.

4. The injection device of claim 3, wherein the mechanical link comprises at least one of a spring, an eccentric element, and an eccentric disc.

5. The injection device of claim 1, wherein the resonating assembly comprises a mechanical link attached to the plunger rod and an oscillator attached to the tubular side, the oscillator being configured to change its RF characteristics based on at least one of a linear and angular position relative to the mechanical link.

6. The injection device of claim 5, wherein the mechanical link comprises a beam that is attached through a membrane to a cantilever of the oscillator.

7. The injection device of claim 1, wherein the resonating assembly comprises a multi-slot patch resonator such that the RF signal comprises at least one of an identifier of the injection device and a medicament type.

8. The injection device of claim 1, wherein the interrogation signal is generated in response to a trigger signal transmitted by the injection device.

9. The injection device of claim 1, wherein the position of the plunger rod is indicative of an amount of medicament within the reservoir.

10. A medicament injection system comprising:
an external device comprising:
a transmitter configured to generate an interrogation signal,
a receiver configured to receive a radio frequency (RF) signal, and
one or more processors configured to process the RF signal and to generate result data to be displayed by the external device; and
an injection device comprising:
a reservoir comprising a wall defining a proximal end, a distal end and a tubular side,
a plunger rod configured to be movable within the reservoir in a direction from the distal end to the proximal end,
a radio frequency (RF) antenna attached to the tubular side and configured to receive an interrogation signal from an external device, and
a resonating assembly configured to receive the interrogation signal from the RF antenna and to generate a modulated RF signal in response to the interrogation signal, the RF signal having a frequency associated with a position of the plunger rod,
wherein the interrogation signal comprises a plurality of interrogation signals received at regular time intervals, and
wherein, in response to receiving the plurality of interrogation signals, the resonating assembly generates a plurality of RF signals, such that a frequency shift between two of the plurality of RF signals is associated with an amount of medicament within the reservoir.

11. The medicament injection system of claim 10, wherein the resonating assembly comprises a magnet attached to the plunger rod and one or more resonators attached to the tubular side and configured to change their RF characteristics based on at least one of a linear and angular position relative to the magnet.

12. The medicament injection system of claim 10, wherein the resonating assembly comprises a mechanical link attached to the plunger rod and a strain sensitive resonator attached to the tubular side, the strain sensitive resonator being configured to change its RF characteristics based on at least one of a linear and angular position relative to the mechanical link.

13. The medicament injection system of claim 12, wherein the mechanical link comprises at least one of a spring, an eccentric element, and an eccentric disc.

14. The injection device of claim 10, wherein the resonating assembly comprises a mechanical link attached to the plunger rod and an oscillator attached to the tubular side, the oscillator being configured to change its RF characteristics based on at least one of a linear and angular position relative to the mechanical link.

15. The injection device of claim 14, wherein the mechanical link comprises a beam that is attached through a membrane to a cantilever of the oscillator.

16. The injection device of claim 10, wherein the resonating assembly comprises a multi-slot patch resonator such that the RF signal comprises at least one of an identifier of the injection device and a medicament type.

17. The injection device of claim 10, wherein the interrogation signal is generated in response to a trigger signal transmitted by the injection device.

18. An injection device comprising:

a reservoir comprising a wall defining a proximal end, a distal end and a tubular side;

a plunger rod configured to be movable within the reservoir in a direction from the distal end to the proximal end;

a radio frequency (RF) antenna attached to the tubular side and configured to receive an interrogation signal from an external device; and a resonating assembly configured to receive the interrogation signal from the RF antenna and to generate a modulated RF signal in response to the interrogation signal, the RF signal having a frequency associated with a position of the plunger rod, wherein the frequency shifts as the position of the plunger rod changes.

19. The injection device of claim 18, wherein the resonating assembly comprises a magnet attached to the plunger rod and one or more resonators attached to the tubular side and configured to change their RF characteristics based on at least one of a linear and angular position relative to the magnet.

20. The injection device of claim 18, wherein the resonating assembly comprises a mechanical link attached to the plunger rod and an oscillator attached to the tubular side, the oscillator being configured to change its RF characteristics based on at least one of a linear and angular position relative to the mechanical link, wherein the mechanical link comprises a beam that is attached through a membrane to a cantilever of the oscillator.

21. A medicament injection system comprising:

an external device comprising:

a transmitter configured to generate an interrogation signal;

a receiver configured to receive a radio frequency (RF) signal; and one or more processors configured to process the RF signal and to generate result data to be displayed by the external device; and an injection device comprising:

a reservoir comprising a wall defining a proximal end, a distal end and a tubular side;

a plunger rod configured to be movable within the reservoir in a direction from the distal end to the proximal end;

a radio frequency (RF) antenna attached to the tubular side and configured to receive an interrogation signal from an external device; and a resonating assembly configured to receive the interrogation signal from the RF antenna and to generate a modulated RF signal in response to the interrogation signal, the RF signal having a frequency associated with a position of the plunger rod, wherein the frequency shifts as the position of the plunger rod changes.

22. The medicament injection system of claim 21, wherein the resonating assembly comprises a magnet attached to the plunger rod and one or more resonators attached to the tubular side and configured to change their RF characteristics based on at least one of a linear and angular position relative to the magnet.

23. The injection device of claim 21, wherein the resonating assembly comprises a mechanical link attached to the plunger rod and an oscillator attached to the tubular side, the oscillator being configured to change its RF characteristics based on at least one of a linear and angular position relative to the mechanical link, wherein the mechanical link comprises a beam that is attached through a membrane to a cantilever of the oscillator.

* * * * *